United States Patent [19]
Miripol et al.

[11] Patent Number: 5,888,328
[45] Date of Patent: Mar. 30, 1999

[54] WELD INTEGRITY TEST KIT

[75] Inventors: Jeffrey E. Miripol, Hockessin, Del.;
Joseph H. Meier, Jr., Bethlehem, Pa.;
Randall L. Graybeal, Rising Sun;
Benjamin A. Hill, Earleville, both of Md.

[73] Assignee: Terumo Medical Corporation, Summerset, N.J.

[21] Appl. No.: 882,854

[22] Filed: Jun. 26, 1997

[51] Int. Cl.⁶ .................................................... B32B 31/00
[52] U.S. Cl. ........................ 156/64; 156/304.2; 156/503
[58] Field of Search .................. 156/64, 158, 304.1, 156/304.2, 304.6, 503

[56] References Cited

U.S. PATENT DOCUMENTS

| | | | |
|---|---|---|---|
| 4,369,779 | 1/1983 | Spencer | 128/213 A |
| 4,461,951 | 7/1984 | Luoma, II et al. | 219/497 |
| 4,476,631 | 10/1984 | Benin | 30/92 |
| 4,501,951 | 2/1985 | Benin et al. | 219/243 |
| 4,610,670 | 9/1986 | Spencer | 604/29 |
| 5,338,689 | 8/1994 | Yves et al. | 436/518 |
| 5,512,432 | 4/1996 | Lapierre et al. | 435/5 |
| 5,749,987 | 5/1998 | Wannebo | 156/64 |

*Primary Examiner*—James Sells
*Attorney, Agent, or Firm*—Andrus, Sceales, Starke and Sawall

[57] ABSTRACT

A kit for testing the integrity of sterile tubing welds made by a sterile tubing welding machine employing welding wafers includes a plurality of tubing samples, and a container having a series of receptacles for holding the tubing samples and the wafers used in the sterile tubing welding machine. A set of instructions is provided for making the sterile tubing welds with the tubing samples in the container, and a data sheet is included for recording particulars of the kit and reporting a weld analysis.

16 Claims, 2 Drawing Sheets

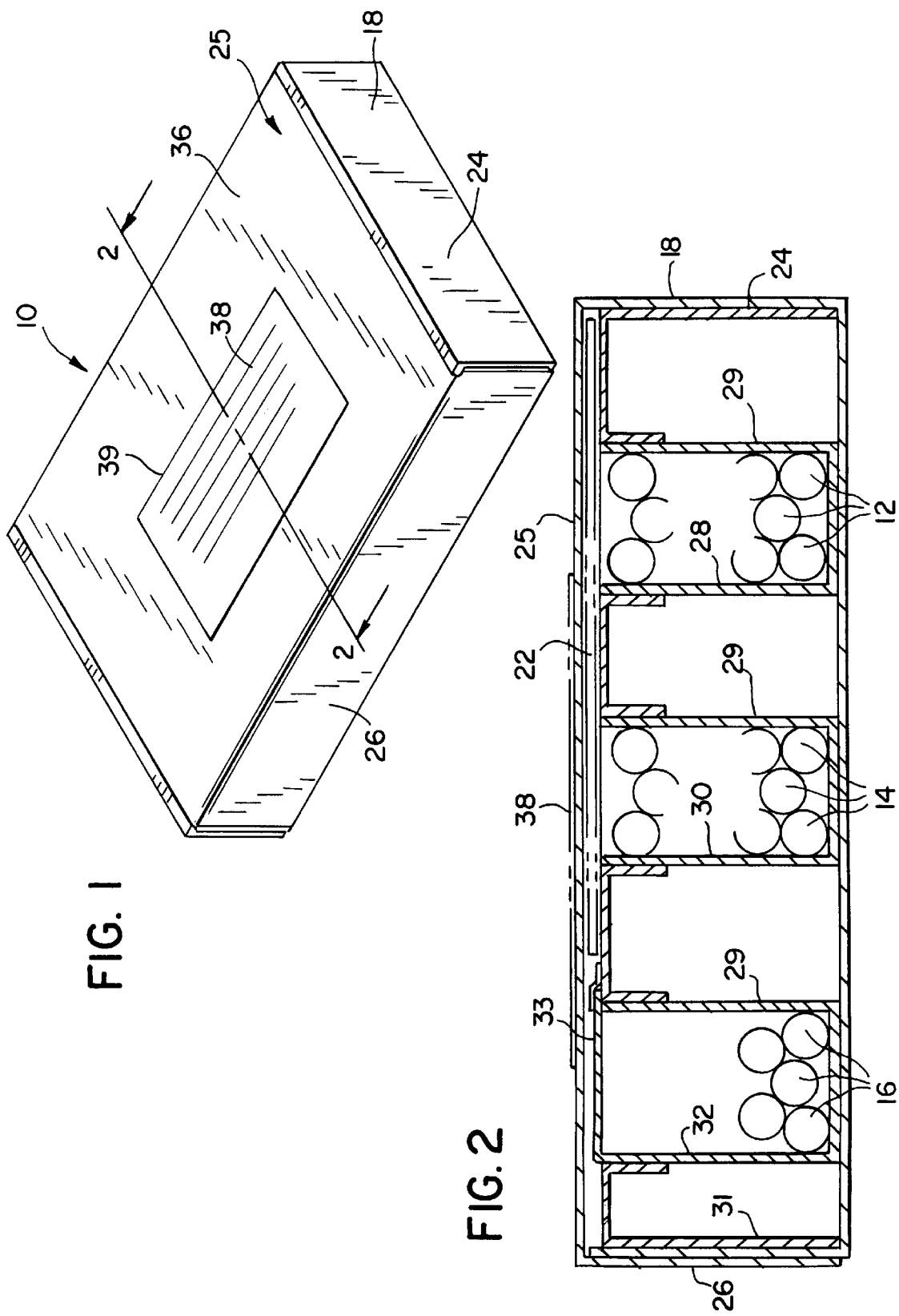

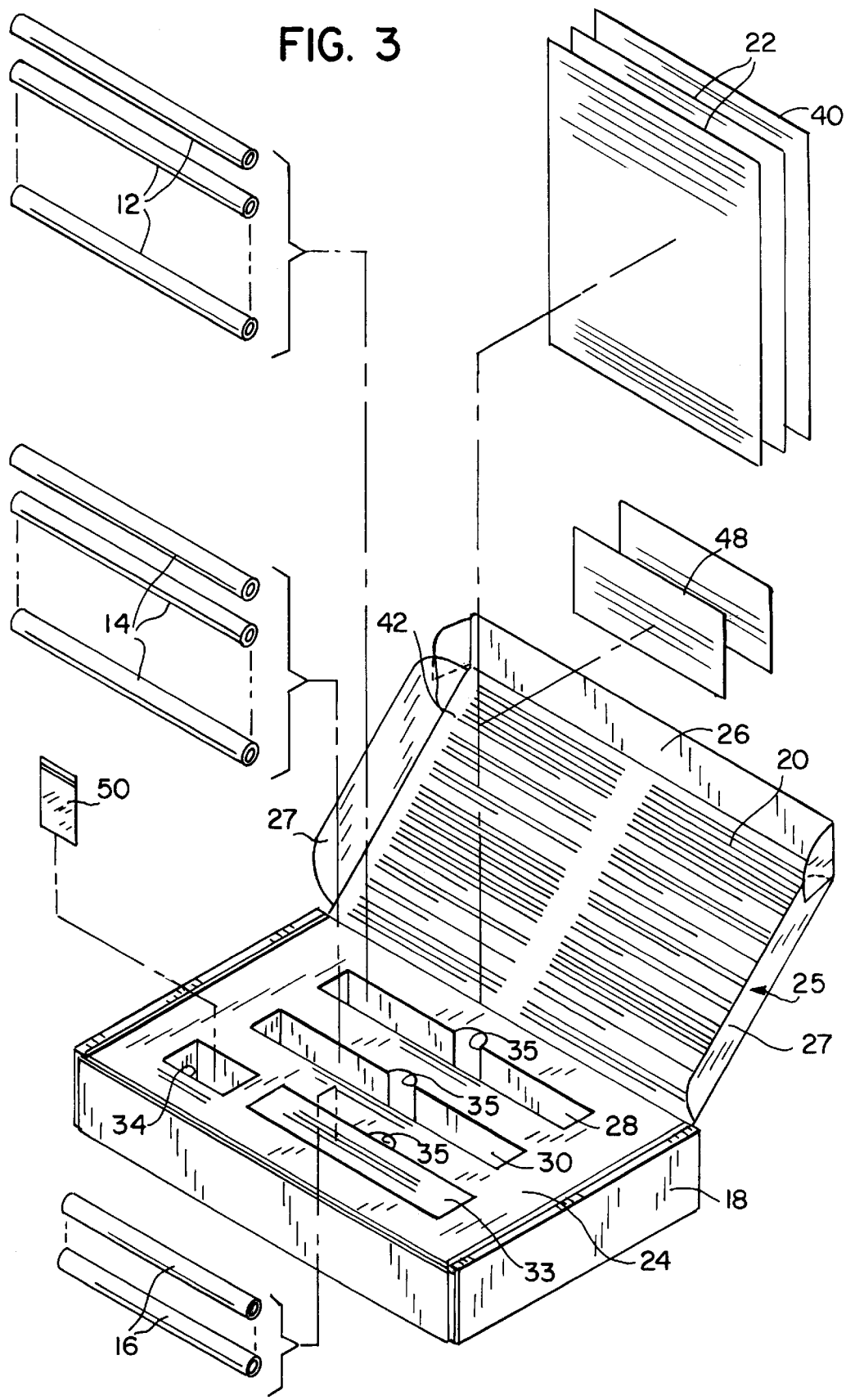

5,888,328

WELD INTEGRITY TEST KIT

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

This invention relates to a kit for testing the integrity of sterile tubing welds made by a sterile tubing welding apparatus.

U.S. Pat. No. 4,610,670 provides a sterile tubing welding machine for sterilely connecting sterile, closed end tubes. The process used in conjunction with the welding machine comprises flattening a section of each tube to urge inside walls of each tube into contact, urging a hot cutting means through the flattened section of each tube thereby temporarily sealing together the inside walls of each tube and providing molten tube ends, aligning the tubes to be connected with each other, joining the desired molten ends of the tubes together to form a joint between the tubes, and cooling the joint and then subjecting it to stress to open the temporary seal in each tube, thereby providing fluid communication between the joint tubes.

The machine covered by the above-noted patent comprises a cutting means, means adapted to heat the cutting means, a pair of mounting blocks adapted to receive, hold and flatten the tubes to be joined, means to provide movement between the blocks and the cutting means to a position such that the cutting means is between the blocks and traversing where the blocks are adapted to hold tubes, means for realigning the blocks to a position where two different tube ends are aligned with and facing each other, means to separate the blocks and the cutting means, and means for urging the mounting blocks together. The tubes to be connected according to this process have closed ends, i.e., the tubes have sealed ends, a tube is connected to a container such as a blood bag or dialysis bag, the tube is connected to a catheter implanted in a patient, or in some other manner the tube ends are closed to the external environment. Other patents which present similar aspects of this machine are disclosed in U.S. Pat. Nos. 4,369,779, 4,461,951, 4,476,631, and 4,501,951.

In the course of using the aforementioned sterile tubing welding machine, customers have requested that the manufacturer provide documentation that satisfies certified good manufacturing practices and quality assurance requirements relating to manufacturing protocols applicable to the welding machine. To provide customers with statistical documentation that their welding machine is operating within the manufacturer's strength specifications and to provide verification that the customer is utilizing the welding machine properly, it would be beneficial to provide a method of verifying the quality of welds made with the welding machine in the form of a convenient feedback system or kit.

What is needed in the art is a comprehensive survey arrangement by which the manufacturer may easily track the working progress of each welding machine so that individual customers can be informed of the quality and strength of welds made by their machines. It is thus desirable to provide a process which can provide for early detection of a possible potential machine failure. It is also necessary to provide a system which affords the manufacturer the opportunity to provide corrective action to improve the welding product according to the specified application identified by the customer. On a broader basis, it would be desirable to create a program which improves the communication between the manufacturer and the customer of the sterile tubing weld machine.

BRIEF SUMMARY OF THE INVENTION

The present invention advantageously provides a monitoring and control plan for enabling customers of sterile tubing welding machines to continuously meet the specifications set forth by the manufacturer. The plan is based on the analysis of specific test welds exchanged between the customer and the manufacturer.

In one aspect of the invention, a kit for testing the integrity of sterile tubing welds made by a sterile tubing welding machine employing welding wafers includes a plurality of tubing samples. A container having a series of receptacles for holding the tubing samples and the wafers used in the sterile tubing welding machine is provided along with instructions for making sterile tubing welds with the tubing samples in the container and a data sheet for recording particulars of the kit and reporting weld analysis. The tubing samples are comprised of generally cylindrical dry tubing and generally cylindrical wet tubing containing albumin or similar proteinaceous or crystalloid solution(s). The container has an openable and closeable lid having an outer face and an inner face with instructions incorporated into the inner face of the lid. A shipping label is secured to the outer face of the lid and a customer label is affixable to the data sheet.

In another aspect of the invention, there is contemplated a method for verifying the quality of sterile tubing welds made with a sterile tube and welding machine employing welding wafers. The method includes the steps of supplying a plurality of dry tubing and wet tubing samples to the user of the welding machine in a closeable container addressed to the user; instructing the user to make dry-to-dry test welds and wet-to-dry test welds according to written instructions included in the container; effecting the test welds according to the written instructions; depositing the test welds and the welding wafers used in making the test welds in the container; completing a data sheet included in the container; enclosing the completed data sheet in the container; and returning the container with the test welds, used wafers and completed data sheet addressed to the original supplier of the container. The method includes the steps of providing control samples in the container, performing weld strength tests, evaluating the welding wafers used in effecting the test welds, documenting the strength of the test welds and reporting statistical documentation regarding the test welds to users of these welding machines.

In yet another aspect of the invention, a feedback system for testing the integrity of sterile tubing welds made with a sterile tubing welding machine employing welding wafers includes a mailable container having a base and a lid pivotally attached to the base and movable between open and closed positions. The lid has an outer face and an inner face, the outer face bearing a removable label arrangement identifying the recipient of the container and the inner face bearing a written sheet of instructions thereon for forming test welds using the welding machine. The container further includes a first receptacle formed with the base for holding a series of wet tubing samples, a second receptacle for holding a series of dry tubing samples, a third receptacle for holding a series of control samples, a fourth receptacle for holding used welding wafers employed in the welding machine and a data sheet for recording particulars of the test welds. The base may be constructed of either cardboard, styrofoam or a lightweight plastic material.

Various other objects, features and advantages of the invention will be made apparent from the following description taken together with the drawings.

BRIEF DESCRIPTION OF THE SEVERAL VIEWS OF THE DRAWINGS

The drawings illustrate the best mode presently contemplated of carrying out the invention. In the drawings:

FIG. 1 is a perspective view of a weld integrity test kit embodying the present invention;

FIG. 2 is a sectional view of the kit taken on line 2—2 of FIG. 1; and

FIG. 3 is an exploded view of the contents of the kit.

DETAILED DESCRIPTION OF THE INVENTION

It should initially be understood that a kit embodying the present invention is used in conjunction with a sterile tubing welding machine in which the tubes to be joined are flattened in an appropriate section so that the inside walls meet. Then the tubes are sequentially or simultaneously melted through by a hot cutting means with molten polymer temporarily sealing the resulting molten tube ends. Since the tubes are temporarily sealed, viable airborne or surface bacteria are unable to find their way inside either of the tubes. The tubes are moved into alignment before or after the heated cutting means is slid away and then the molten tube ends are pushed together to form a joint. The joint is briefly cooled and then subjected to slight stress to open the temporary seal on each tube. The joint is sound and strong and a number of additional joints can be made in subsequent sterile connections with the same tube. Furthermore, each subsequent connection can be made at exactly the same point on the tube. The process can be used to make more than one joint at a time by using multiple (more than two) tubes and multiple tube slots. The tubes to be connected in the process of the invention have closed ends, i.e., the tubes have sealed ends, the tube is connected to a container such as a blood bag or dialysis bag, the tube is connected to a catheter implanted in a patient, or in some other manner the tube ends are closed to the external environment.

Referring to FIGS. 1–3, a kit supplied by the manufacturer to the customer for testing the integrity of sterile tubing welds made by the above-described welding machine is generally identified by the reference numeral 10. The kit comprises a plurality of wet tubing samples 12, dry tubing samples 14 and control samples 16, a mailable container 18, printed instructions 20 for making sterile welds with the samples 12, 14, in the container 18 and a multiple-page data sheet 22 for recording particulars of the kit 10.

All of the samples 12, 14, 16 are typically cylindrical segments of plastic tubing such as polyvinylchloride (PVC), C-Flex or other suitable material having a length of approximately 4 inches to 6 inches and an outer diameter of 0.152 to 0.220 inches. The wet tubing samples 12 have closed ends and carry a liquid such as albumin or similar proteinaceous or crystalloid solution(s) therein. The dry tubing samples 14 are open-ended. The control samples 16 are identical to the dry tubing samples 14 and are included in the kit as a reference only against which the samples 12 and 14 may be compared after they are welded. For example, the control samples 16 supplied with the kit 10 will have a certain pull strength at a particular environmental condition such as relative humidity. It is on this basis that the tubing samples may be accurately compared once the welds have been affected.

The container 18 includes a base 24 and a lid 25 which is pivotally connected to the base 24 and movable between open and closed positions. The lid 25 is provided with a conventional front flap 26 and side flaps 27 which tuck into slots formed in the base 24. The container 18 is preferably constructed of cardboard, styrofoam or another lightweight plastic material, and is typically 12 inches in length, 8 inches in width and 2 inches in height. The base 24 is formed with a series of four receptacles, each of which is designed to retain tubing samples 12, 14, 16 or cutting wafers (not shown) used in the welding machine. In particular, a first receptacle 28 is formed substantially along the length of the base 24 at the top thereof for holding a series of wet tubing samples 12 therein. The first receptacle 28 is generally 8 inches in length, 1 inch in width and almost 2 inches in depth. A second receptacle 30 having similar dimensions as the first receptacle is formed in the base 24 substantially parallel to and forward of the first receptacle 28 for holding a series of dry tubing samples 14. A third receptacle 32 is formed in the base 24 substantially parallel to and forward of the second receptacle 30 for holding a series of control samples 16. The third receptacle 32 is shorter in length than the first and second receptacles 28, 30. The third receptacle 32 is provided with a hinged cover 33 for covering the control samples 16. Suitable indicia on the cover 33 specifically warns the user of the kit 10 not to open the flap 33 and to return control samples 16, as is, with the kit 10. A fourth receptacle 34 is formed in the base 24 forward of the second receptacle 30 and to the left of the third receptacle 32 for holding a series of the welding wafers used in forming the sterile welds with the welding machine. Each of the receptacles 28, 30, 32 is provided with finger slots 35 to facilitate the handling of samples 12, 14, 16. Suitable indicia identifying the contents of each receptacle 28, 30, 32, 34 is provided on the base 24. Empty chambers 29, 31 are formed on the forward and rearward sides of the receptacles 28, 30, 32 and 34.

The lid 25 pivotally attached to the base 24 has an outer face 36 which bears a pre-addressed label 38 as part of an airway bill 39 identifying the name and address of the manufacturer to whom the kit 10 will be returned. The lid 25 also has an inner face 42 upon which is included the printed list 20 of instructions for making test welds using the tubing samples 12, 14. Upon opening the lid 25 to expose the tubing samples 12, 14, the customer will also find enclosed the printed data sheet 22 to be completed after the welds are made. In addition, instructions 40 for filling out the airway bill 39 are also included. The data sheet 22 will include an affixable customer label 48, certain particulars of the kit 10 including the serial number of the welding machine, and analysis feedback to be sent back to the customer reporting the findings of the manufacturer having examined the welds made with the kit 10.

In use, the customer having requested the kit 10 typically receives the shipped enclosed container 18 in a mailing envelope. Upon removing the kit 10 from the mailing envelope, the customer opens the container 18 and follows the welding instructions 20 listed on the inner face 42 of lid 25 using the tubing samples 12, 14 in the receptacles 28, 30, and the customer's welding machine. Once the sterile tubing welds have been completed, they are returned to their original receptacles 28, 30 and enclosed in the container 18 along with the welding wafers used in perfecting the welds. The welding wafers are preferably placed in a small plastic bag 50 included in the fourth receptacle 34. The Customer Information Section of the data sheet 22 is completed by the customer, placed on the base 24 and the lid 25 is closed either by a locking structure on the base 24 or adhesive means on the lid 25. After the customer completes the partially pre-addressed shipping label 38 as per the instructions for completing the airway bill 39 that is already on the container 18, the kit 10 is ready to be mailed back to the manufacturer who will perform weld strength tests on the welded samples and complete a statistical report enabling the customer to better conform with the specifications issued with the welding machines.

It should be understood that the present invention helps the customer satisfy various quality assurance standards relating to the use of the sterile tubing welding machine. The present invention further assists the manufacturer in monitoring the performance of weld strength by welding machine serial number. In addition, the present invention establishes a feedback system which informs the manufacturer about the particular applications of the welding machine and the customers about improved welding practices.

While the invention has been described with reference to a preferred embodiment, those skilled in the art will appreciate that certain substitutions, alterations and omissions may be made without departing from the spirit thereof. Accordingly, the foregoing description is meant to be exemplary only, and should not be deemed limitative on the scope of the invention set forth with following claims.

We claim:

1. A method for verifying the quality of sterile tubing welds made with a sterile tubing welding machine employing welding wafers, the method comprising the steps of:

supplying a plurality of dry tubing and wet tubing samples to the user of the welding machine in a closeable container addressed to the user;

instructing the user to make dry-to-dry test welds and wet-to-dry test welds according to written instructions included in the container;

effecting the test welds according to the written instructions;

depositing the test welds and the welding wafers used in making the test welds in the container;

completing a data sheet included in the container;

enclosing the completed data sheet in the container; and returning the container with the test welds, used wafers and completed data sheet addressed to the original supplier of the container.

2. The method of claim 1 including the step of providing control samples in the container.

3. The method of claim 1, including the step of performing weld strength tests.

4. The method of claim 1, including the step of evaluating the welding wafers used in effecting the test welds.

5. The method of claim 1, including the step of documenting the strength of the test welds.

6. The method of claim 1, including the step of reporting statistical documentation regarding the test welds to users of the welding machine.

7. A kit for testing the integrity of sterile tubing welds made by a sterile tubing welding machine employing welding wafers, the kit comprising:

a plurality of tubing samples;

a container having a series of receptacles for holding the tubing samples and the wafers used in the sterile tubing welding machine;

instructions for making sterile tubing welds with the tubing samples in the container; and a data sheet for recording particulars of the kit and reporting weld analysis.

8. The kit of claim 7, wherein the tubing samples are comprised of generally cylindrical dry tubing and generally cylindrical wet tubing containing albumin or similar proteinaceous or crystalloid solution(s).

9. The kit of claim 7, wherein the container has an openable and closeable lid having an outer face and an inner face.

10. The kit of claim 9, wherein the instructions are incorporated into the inner face of the lid.

11. The kit of claim 9, including a shipping label which is secured to the outer face of the lid.

12. The kit of claim 7, including a customer label which is affixable to the data sheet.

13. A feedback system for testing the integrity of sterile tubing welds made with a sterile tubing welding machine employing welding wafers, the system comprising:

a mailable container having a base and a lid pivotally attached to the base between open and closed positions, the lid having an outer face and an inner face, the outer face bearing a removable label arrangement as part of an airway bill identifying the recipient of the container, and the inner face bearing a written sheet of instructions thereon for forming test welds using the welding machine, the container further including:

a first receptacle formed in the base for holding a series of wet tubing samples, a second receptacle formed in the base for holding a series of dry tubing samples, a third receptacle formed in the base for holding a series of control samples, a fourth receptacle formed in the base for holding used welding wafers employed in the welding machine, a data sheet for recording particulars of the test welds, and instructions for completing the airway bill.

14. The feedback system of claim 13, wherein the base is constructed of cardboard.

15. The feedback system of claim 13, wherein the base is constructed of styrofoam.

16. The feedback system of claim 13, wherein the base is constructed of lightweight plastic material.

* * * * *